United States Patent [19]
Kamen et al.

[11] Patent Number: 5,578,012
[45] Date of Patent: Nov. 26, 1996

[54] MEDICAL FLUID PUMP

[75] Inventors: Dean L. Kamen, Bedford; Kevin L. Grant, Dover; Valentine Faust, Bow; Richard J. Lanigan, Concord, all of N.H.

[73] Assignee: Deka Products Limited Partnership, Manchester, N.H.

[21] Appl. No.: 427,142

[22] Filed: Apr. 24, 1995

[51] Int. Cl.⁶ .................................................. F04D 29/00
[52] U.S. Cl. ................................. 604/151; 623/3; 600/16
[58] Field of Search .............................. 604/131, 146, 604/151; 600/16; 623/3; 415/206

[56] References Cited

U.S. PATENT DOCUMENTS

| | | |
|---|---|---|
| 2,428,912 | 10/1947 | Hulsberg . |
| 2,449,772 | 9/1948 | Gilman . |
| 2,472,010 | 5/1949 | Gilman . |
| 3,139,832 | 7/1964 | Saunders ............................ 623/3 X |
| 3,487,784 | 1/1970 | Rafferty et al. . |
| 3,559,644 | 2/1971 | Stoft et al. . |
| 3,617,153 | 11/1971 | Mowry ............................... 417/241 |
| 3,864,055 | 2/1975 | Kletschka et al. ...................... 415/1 |
| 3,915,351 | 10/1975 | Kiralfy ............................... 222/385 |
| 4,121,895 | 10/1978 | Watson ............................... 417/104 |
| 4,142,523 | 3/1979 | Stegeman . |
| 4,412,786 | 11/1983 | Perry ................................ 417/241 |
| 4,482,346 | 11/1984 | Reinicke ............................ 604/152 |
| 4,925,451 | 5/1990 | Amendolia .......................... 604/246 |
| 5,178,515 | 1/1993 | Tsuchiya et al. ..................... 600/16 X |
| 5,193,977 | 3/1993 | Dame ................................ 415/206 |
| 5,346,458 | 9/1994 | Affeld .............................. 623/3 X |
| 5,443,503 | 8/1995 | Yamane .............................. 623/3 |

FOREIGN PATENT DOCUMENTS

| | | | |
|---|---|---|---|
| 599138 | 6/1994 | European Pat. Off. ............... | 604/151 |
| 2918325 | 1/1980 | Germany . | |
| 404231065 | 8/1992 | Japan ............................. | 604/151 |
| 404212370 | 8/1992 | Japan ............................. | 604/151 |
| 1444562 | 12/1988 | U.S.S.R. . | |
| 837961 | 6/1960 | United Kingdom . | |
| 93/021976 | 11/1993 | WIPO ............................. | 604/151 |
| 95/00185 | 1/1995 | WIPO ............................. | 604/151 |

*Primary Examiner*—Sam Rimell
*Attorney, Agent, or Firm*—Bromberg & Sunstein

[57] ABSTRACT

A medical pump apparatus including an internally sterile pumping chamber having a flexible diaphragm forming a wall portion and a drive rod extending through the diaphragm in a rotating vane disposed within the pumping chamber. A motor rotates a revolving hook which engages the drive rod to drive the vane within the pumping unit. The pumping chamber is isolated from the motor by the fluidtight attachment of the drive rod through the flexible diaphragm. Fluid is pumped into the inlet of pumping chamber through the hollow shaft of the vane and out through a fluid conduit of the vane, subsequently out the outlet of the pumping chamber.

18 Claims, 3 Drawing Sheets

MEDICAL FLUID PUMP

BACKGROUND OF THE INVENTION

The present invention relates to medical fluid pumps, in particular, a sterile centrifugal pump for pumping pressurized irrigating fluid into a joint undergoing arthroscopic surgery.

Whenever fluids are being pumped into a patient, it is essential that the fluid move only through a sterile environment. Therefore, for a pump to be useful in this environment, it is necessary that the mechanics of the pump be kept isolated from the fluid pathway.

U.S. Pat. No. 3,864,055 (Kletschka et al.) discloses a medical fluid pump in which a rotator spins within a chamber causing fluid to be propelled through the outlet of the chamber. The rotator within the chamber is mounted on a drive shaft that is journalled in a bearing. The shaft journalled within the bearings requires a precision fit which adds to the cost of such a pump. O-ring seals are used to maintain the chamber leak proof. The O-ring seals will work so long as they have not worn to the point where leaking may be possible. U.S. Pat. No. 5,178,515 (Tsuchya et al.), on the other hand, discloses a medical pump that is driven through a diaphragm. A rocker is connected to a shaft mounted through a diaphragm. The shaft is driven so as to rock the rocker within the chamber causing a rotating flow of fluid through the chamber and out through its outlets. In accordance with German Offenlegungsschraft 2918325 (Sempio), a pump chamber fed by an inlet has a ring which is swung around within the chamber causing the fluid to be forced out through the outlet. The drive shaft for the ring appears to be suspended within a diaphragm for hermetically sealing the chamber from the drive mechanism.

SUMMARY OF THE INVENTION

The present invention is directed to a medical fluid pump with a sterile disposable centrifugal pump unit. The pump unit provides a rotating vane or impeller within an internally sterile pumping chamber. The vane rotates about a hollow shaft that is in fluid communication with an inlet to the pumping chamber. A flexible diaphragm forms a wall portion of the pumping chamber. A drive rod extends through the diaphragm so that one end of the rod engages the vane at a position on the vane radially offset from the axis of rotation of the hollow shaft. Rotation of the vane is achieved by revolving the end of the drive rod that extends out from the pumping chamber. The rotation of the vane increases fluid pressure within the pumping chamber causing fluid to be forced out through an outlet. Fluid from a fluid source is drawn in through the inlet into the hollow shaft and out the ends of the rotating vane. The mechanical apparatus for operating the pumping unit will generally include a motor and a revolving hook for engaging the exterior end of the drive rod.

The fluidtight attachment of the drive rod through the diaphragm maintains the pumping unit sealed beneath the pump motor so that contaminants may not enter the pumping chamber. The pumping unit is advantageously a low-cost disposable unit. Other objects and advantages of the present invention will become apparent during the following description of the presently preferred embodiment of the invention taken in conjunction with the drawings.

DETAILED DESCRIPTION OF THE PREFERRED EMBODIMENTS

Figure 1:
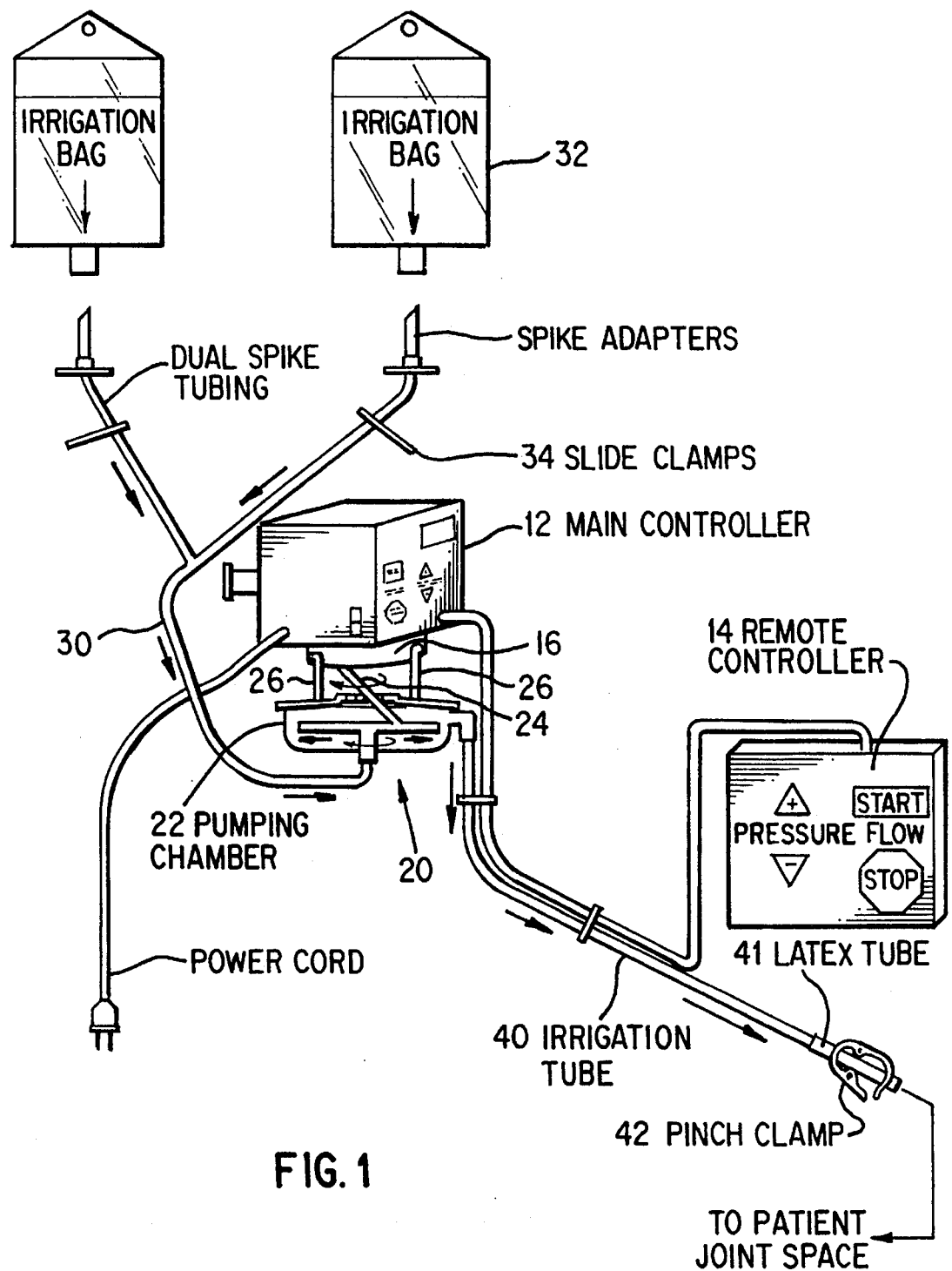
FIG. 1 provides a layout of the medical pump apparatus of the present invention.

Referring now to FIG. 1, the permanent portions of the medical pump apparatus include a motor 10 electrically controlled by a main controller 12. If desired, a remote control 14 may be included using a hard wire or wireless connection to the main controller. A revolving hook 16 turns in connection to the motor 10. The hook may be an open loop, a closed loop, a slot or other equivalent engagement mechanism for revolving a drive rod. The main controller 12 or remote 14 are used to operate the speed at which the revolving hook 16 revolves. An increase in speed of the revolving hook increases the fluid pressure in the pump.

A disposable pumping unit 20 is provided for removable attachment to the motor 10. The pumping unit includes a pumping chamber 22 suspended beneath the motor 10. Any conventional attachment such as the hooks 26 shown in FIG. 1 may be used to suspend the pumping unit beneath the motor. The pumping chamber 22 has a drive rod 24 extending out from it. The drive rod 24 engages the revolving hook 16. The pumping chamber 22 is internally sterile and remains that way as it has been sealed to isolate it from the non-sterile environment.

The disposable pumping unit 20 further includes an inlet tube 30 for providing fluid into the chamber 22. The fluid source for the pump may be provided by fluid bags suspended from I.V. poles. As shown in FIG. 1, the inlet tube 30 may be provided with a Y connection so that two bags may be connected. When one bag is emptied, the other bag can be used to provide the fluid to the inlet tube 30. Slide clamps 34 on the tube 30 allow for switching from one bag 32 to the other. The empty bag can then be replaced by a full bag of fluid so that the pumping process need not be interrupted by an empty bag.

An outlet tube 40 is attached to an outlet of the pumping chamber 22. The inlet tube 30 and the outlet tube 40 may be made from PVC tubing. An end connector tube 41 may be attached to the output end of the outlet tube 40 for connecting the outlet tube 40 to arthroscopes, input cannulas or the like. A pinch clamp 42 on the end connector tube 41 permits medical personnel to hold the tube closed until an appropriate time. The pumping apparatus of the invention is particularly well suited for use in delivering irrigating fluid under pressure to a joint being operated on arthroscopically. However, other medical pumping procedures may also benefit from use of the pumping apparatus of the present invention. Since the sterility of fluids being used in operations or for infusions into a patient is extremely important, it is advantageous that in accordance with the present invention, the pumping unit and attached tubes are provided as an internally sterile disposable unit. While the motor and controller can be reused with other pumping units, each patient may receive a new clean pumping unit. As such, a labor and energy intensive sterilization procedure can be avoided.

Figure 2:
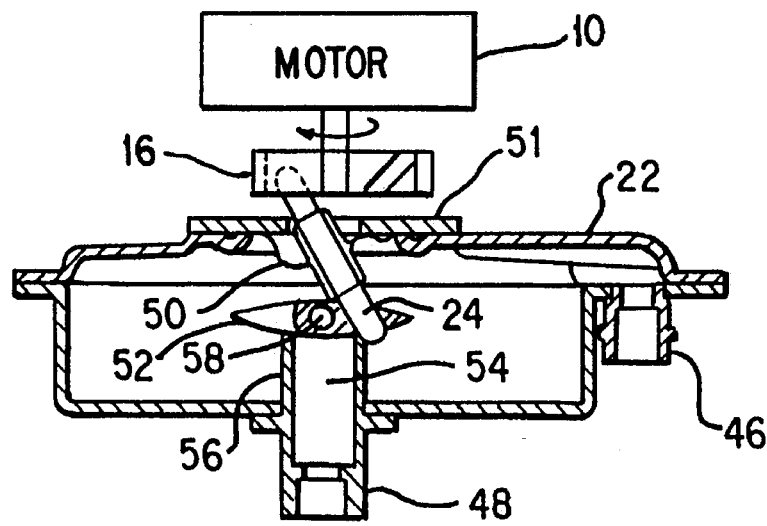
FIG. 2 is a side view of the motor and pumping unit of the present invention with the pumping unit in cross section.

The pumping unit of the present invention shall be described in more detail with respect to FIG. 2. The pumping chamber 22 is internally sterile. The chamber is made of a low cost material that is sterilizable. One suitable plastic material for the pumping chamber is acrylic, such as Cyrolite. An outlet 46 and an inlet 48 provide the only means by which fluid may enter or leave the pumping chamber 22. The inlet 48 is located at the bottom of the pumping chamber 22 opposite from a diaphragm 50. The diaphragm 50 holds the drive rod 24. A disk ring 51 may be attached to the chamber wall to fit above the diaphragm 50. The disk ring 51 then prevents the diaphragm 50 from ballooning up under pressure. The drive rod 24 is used for transmitting the mechanical energy from the motor 10 to a rotating vane 52 within the pumping chamber. The vane 52 rotates on a hollow shaft 54. The hollow shaft 54 is disposed within a tubular channel 56 which leads to the inlet 48. Thus, the hollow shaft 54 is in fluid communication with the inlet 48. The vane 52 includes a fluid conduit perpendicular to the tubular channel 56 that extends from one end of the vane to the other end. As the vane 52 rotates about the axis of the hollow shaft 54, fluid is drawn up through the inlet 48 into the hollow shaft 54 and out both ends of the vane 52. The fluid travels through the hollow shaft 54 into the fluid conduit 58.

Figure 3:
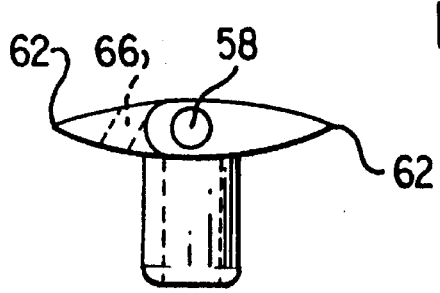
FIG. 3 is an end view of the rotating vane used in the pumping unit of the present invention.
Figure 4:
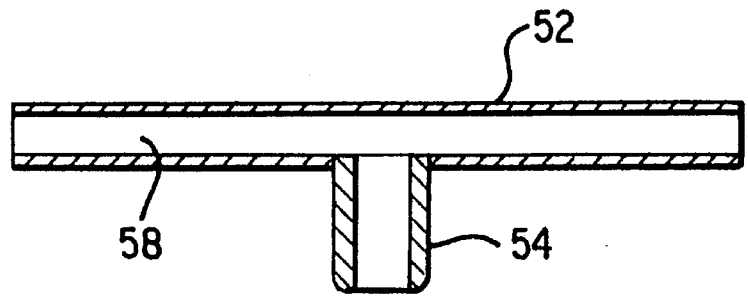
FIG. 4 is a cross sectional side view of the rotating vane of FIG. 3.
Figure 5:
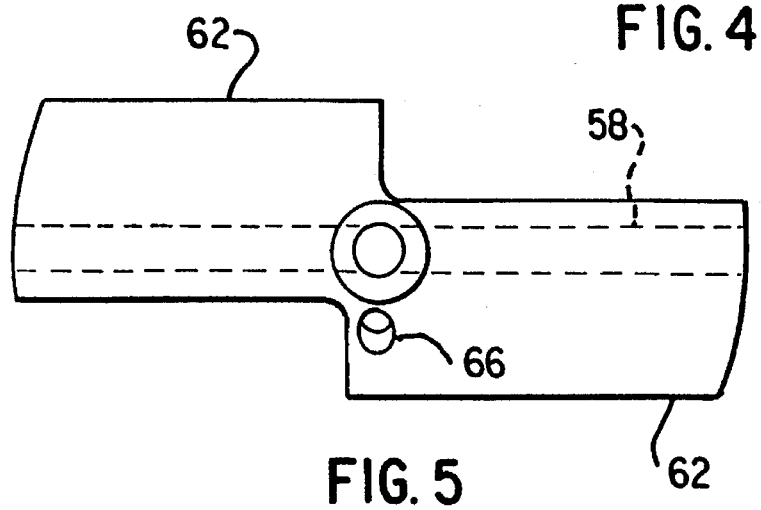
FIG. 5 is a bottom view of the rotating vane of FIG. 3.

The construction of the rotating vane 52 (or impeller) shall now be described in greater detail with respect to FIGS. 3, 4 and 5. The purpose of the rotating vane 52 is to increase fluid pressure within the pumping chamber 22. However, it is desirable that the rotation of the vane avoids to the extent possible the creation of turbulence within the pumping chamber 22. Turbulence increases drag. By reducing drag on the rotating vane, the amount of power consumed by the pump motor can be reduced. To reduce drag and power consumption, a hydrodynamic design of the vane such as shown in FIG. 3 is desirable. The rotating vane 52 of the present invention is formed by a pair of wings. Each wing has an outer narrow edge 62. The wing expands gradually from edge 62 to a thick portion surrounding the fluid conduit 58. The edge at the thick portion acts as the leading edge of the wing and has a radius of curvature that is larger than the radius of the fluid conduit 58. The curve of the wing on the upper side and lower side should be made approximately equal so that the rotation of the vane does not create lifting forces which pull the vane out of the tubular chamber 56. The two wings of the vane extend in opposite directions from the hollow shaft 54. The narrow edge 62 of each of the wings is directed so that upon rotation of the vane, the narrow edge 62 of each wing is the trailing edge of the rotating wing. As shown in FIG. 4, the fluid conduit 58 is in fluid communication with the hollow shaft 54. The fluid conduit 58 is perpendicularly disposed relative to the hollow shaft 54. The fluid conduit 58 extends from one end of the vane 52 to the opposite end. Fluid is drawn in through the hollow shaft 54 and splits into two directions, one towards one end of the vane and the other towards the other end of the vane.

The vane 52 is provided with an angled slot 66. The angled slot 66 is radially offset from the hollow shaft 54. The slot 66 is provided for engaging the drive rod 24. The angled slot 66 is lightly larger in diameter than the drive rod 24 so that the drive rod 24 freely fits within the angled slot and may rotate within the slot. An increased diameter of 0.015" for the slot has been found to work sufficiently well. As the motor revolves one end of the drive rod 24, the other end of the drive rod 24 revolves around the hollow shaft. In this manner, the vane 52 is caused to rotate about the shaft. The hollow shaft 54 rotates within the tubular inlet chamber 56. The fit of the hollow shaft 54 within the chamber 56 is a clearance fit so that the fluid in the pumping chamber seeps around the shaft reducing friction during rotation. Friction is further reduced by making at least one of the vane 52 and the tubular inlet chamber out of a low coefficient of friction material. In the presently preferred embodiment, the vane 52 is made of Delrin. The hollow shaft 54 has an outer diameter of 0.408 inches and the inlet 48 has an inner diameter of 0.416 inches.

Figure 6:
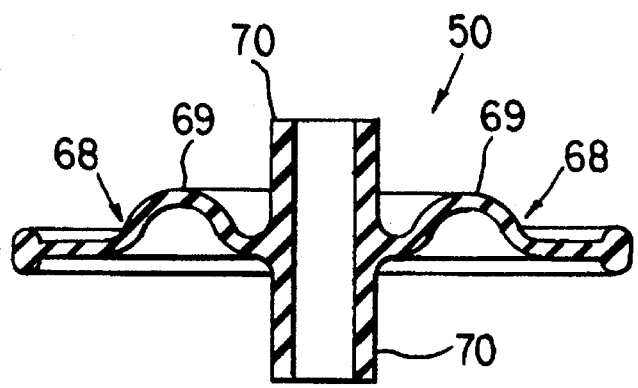
FIG. 6 is a cross sectional view of the diaphragm used in the wall of the pumping chamber of the present invention.

The diaphragm 50 which holds the drive rod in a fluidtight sealing attachment suspended above the rotating vane 52 is shown in greater detail in FIG. 6. The diaphragm 50 includes a web 68 which forms a portion of the wall of the pumping chamber 22. The presently preferred web 68 includes an annular wave or rib 69. The rib 69 bumps up against the disk ring 51. A tubular sleeve 70 is suspended in the center of the web 68. The tubular sleeve 70 slides snugly over the drive rod 24 to form a fluidtight engagement therewith. The drive rod 24 may include a bump just beyond the opposite ends of the tubular sleeve 70 to provide stops that prevent the sleeve from moving along the drive rod. The drive rod 24 of the presently preferred embodiment is made of Delrin. The diaphragm of the presently preferred embodiment is made of urethane, such as Pelethane. As the drive rod 24 is revolved by the hook 16, the web 68 bends and stretches to permit the drive rod to wobble yet holding the drive rod generally in the center area of the diaphragm. The drive rod is held tightly within the tubular sleeve and is not permitted to rotate therein. Therefore, the engagement of the drive rod 24 with the revolving hook 16 and within the angular slot 66 must permit rotation.

Figure 7:
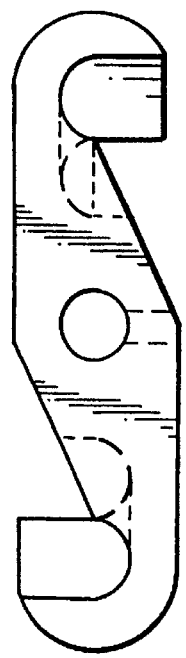
FIG. 7 is a plan view of the revolving hook attached to the motor of the present invention.
Figure 8:
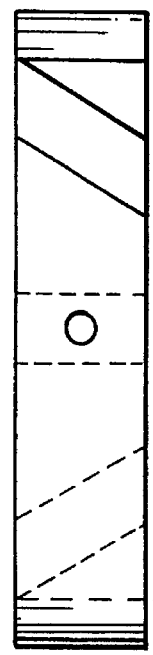
FIG. 8 is a side view of the revolving hook of FIG. 7.

The revolving hook 16 is shown at FIGS. 7 and 8. In the presently preferred embodiment, the revolving hook is aluminum and is provided with two hook portions either of which may be used to engage the external end of the drive rod 24. The hook has a slot which is angled to accommodate the end of the drive rod 24. The angle of the slot is provided to accommodate the angle at which the drive rod is skewed between the center of the diaphragm and the end engaging the hook 16. Preferably, this angle should be the same as the angle of the slot 66 in the vane 52.

The pump of the present invention operates on the principal of a centrifugal pump. The fluid pressure within the chamber is proportional to the square of the speed of the rotation of the vane. As the pressure of the fluid in the chamber increases, the pressure of the fluid delivered through the outlet tube increases. Pumping rate can be increased by increasing the speed of rotation of the vane. The present invention advantageously provides a low-cost disposable pumping unit which is internally sterile and is provided in a fluidtight isolated relationship from the motorized control for the pump.

Of course, it should be understood that various changes and modifications to the preferred embodiment described above will be apparent to those skilled in the art. For example, numerous hydrodynamic vane designs may be used within the scope of the present invention. Likewise, the revolving hook may be a loop, slot or other revolving entity to capture the end of the drive rod as the motor rotates. These and other changes may be made without departing from the spirit and scope of the invention and without diminishing its attendant advantages. It is therefore intended that such changes and modifications be covered by the following claims.

We claim:

1. A pumping unit comprising:
   an internally sterile pumping chamber having an inlet and an outlet;
   a vane mounted for rotation about a hollow shaft, the hollow shaft being in fluid communication with the inlet of said pumping chamber and said vane having a fluid conduit extending therethrough in fluid communication with the hollow shaft;
   a flexible diaphragm forming a wall portion of said pumping chamber; and
   a drive rod extending through said diaphragm so that one end of said rod engages said vane within said pumping chamber at a position on said vane radially offset from the axis of rotation of the hollow shaft and an other end extends out of said pumping chamber, said drive rod being in a fixed fluidtight attachment with said diaphragm.

2. The pumping unit of claim 1 wherein said flexible diaphragm includes a tubular sleeve suspended by a flexible web and wherein said drive rod is fixedly attached in fluidtight engagement within the tubular sleeve.

3. The pumping unit of claim 1 wherein the inlet comprises a tubular channel and the hollow shaft rotates journalled within the tubular channel.

4. The pumping unit of claim 1 wherein said vane is formed by a pair of wings and the fluid conduit extends perpendicular to the hollow shaft from one end of the vane to the opposite end of the vane.

5. The pumping unit of claim 1 wherein the fluid conduit of said vane extends from one end of the vane to an opposite end of the vane and wherein said vane is formed by one wing extending from the hollow shaft to the one end of the vane and a second wing extending from the hollow shaft to the opposite end of the vane, each of the first and second wings being oppositely directed with a thick portion surrounding the fluid conduit progressively narrowing to a trailing edge.

6. The pumping unit of claim 1 wherein said vane includes an angled slot radially offset from the hollow shaft for engaging said drive rod.

7. The pumping unit of claim 1 wherein the inlet is disposed in said pumping chamber opposite from said flexible diaphragm.

8. A medical pump apparatus comprising:
   a motor;
   a revolving hook connected for rotation to said motor;
   an internally sterile pumping chamber having an inlet, an outlet and one end of a drive rod extending out from a diaphragm so that the one end of the drive rod engages said revolving hook to cause the one end of the drive rod to revolve; and
   a rotatable vane disposed within said pumping chamber and engaged by an opposite end of the drive rod to cause rotation of said vane about an axis, said rotatable vane including a hollow shaft concentric with the axis of rotation, the hollow shaft being in fluid communication with the inlet of said pumping chamber such that rotation of said rotatable vane increases fluid pressure within said pumping chamber to force fluid out through the outlet and draw fluid in through the inlet into the hollow shaft and out of said rotatable vane.

9. The medical pump apparatus of claim 8 wherein said rotatable vane further comprises a slot radially offset from the hollow shaft for engaging with the opposite end of the drive rod.

10. The medical pump apparatus of claim 8 wherein the diaphragm includes a tubular sleeve suspended by a flexible web and wherein the drive rod is fixedly attached in fluidtight engagement within the tubular sleeve.

11. The medical pump apparatus of claim 8 wherein the inlet comprises a tubular channel and the hollow shaft rotates journalled within the tubular channel.

12. The medical pump apparatus of claim 8 wherein said rotatable vane comprises a first and second wing extending perpendicular to the hollow shaft in opposite directions from the hollow shaft.

13. The medical pump apparatus of claim 12 wherein said rotatable vane further comprises a fluid conduit in fluid communication with the hollow shaft extending perpendicular to the hollow shaft the full length of the first and second wings.

14. The medical pump apparatus of claim 13 wherein each of the first and second wings are arranged with a thick portion surrounding the fluid conduit progressively narrowing to a trailing edge.

15. The medical pump apparatus of claim 8 wherein the inlet is disposed in said pumping chamber opposite from the diaphragm.

16. The medical pump apparatus of claim 8 further comprising a fluid source elevated above said pumping chamber and a tube connecting said fluid source to the inlet of said pumping chamber.

17. A method for controlling the flow of fluid into a patient comprising the steps of:
   directing fluid into a shaft of a rotatable vane mounted within a pumping chamber for axial rotation about the shaft;
   revolving an end of a rod extending from a diaphragm forming a wall of the pumping chamber so as to revolve an opposite end of said rod engaged with the rotatable vane at a position radially offset from the shaft to cause the rotatable vane to rotate; and
   the rotation of the vane causing the fluid to be pushed out of the pumping chamber through a tube to a patient.

18. The method of claim 17 further comprising adjusting the speed of revolving the end of the rod to control the amount of fluid pressure in the pumping chamber.

* * * * *